United States Patent
Bezuhly

(10) Patent No.: US 9,815,317 B2
(45) Date of Patent: Nov. 14, 2017

(54) SURGICAL MARKER

(71) Applicant: Dalhousie University, Halifax, Nova Scotia (CA)

(72) Inventor: Michael Bezuhly, Halifax (CA)

(*) Notice: Subject to any disclaimer, the term of this patent is extended or adjusted under 35 U.S.C. 154(b) by 163 days.

(21) Appl. No.: 14/552,348

(22) Filed: Nov. 24, 2014

(65) Prior Publication Data

US 2015/0086258 A1 Mar. 26, 2015

Related U.S. Application Data

(63) Continuation of application No. PCT/CA2013/050396, filed on May 24, 2013.

(60) Provisional application No. 61/651,451, filed on May 24, 2012.

(51) Int. Cl.
| | |
|---|---|
| *B43K 24/06* | (2006.01) |
| *B43K 24/14* | (2006.01) |
| *A61B 90/00* | (2016.01) |
| *B43K 8/00* | (2006.01) |
| *B43K 8/02* | (2006.01) |
| *B43K 8/03* | (2006.01) |
| *B43K 13/00* | (2006.01) |
| *B43K 23/008* | (2006.01) |
| *B43K 24/12* | (2006.01) |
| *B43K 24/16* | (2006.01) |
| *B43K 1/01* | (2006.01) |
| *B43K 1/12* | (2006.01) |

(52) U.S. Cl.
CPC ............ *B43K 24/06* (2013.01); *A61B 90/39* (2016.02); *B43K 1/01* (2013.01); *B43K 1/12* (2013.01); *B43K 8/003* (2013.01); *B43K 8/02* (2013.01); *B43K 8/03* (2013.01); *B43K 13/005* (2013.01); *B43K 23/008* (2013.01); *B43K 24/12* (2013.01); *B43K 24/14* (2013.01); *B43K 24/16* (2013.01); *A61B 2090/395* (2016.02); *A61B 2090/3966* (2016.02)

(58) Field of Classification Search
CPC combination set(s) only.
See application file for complete search history.

(56) References Cited

U.S. PATENT DOCUMENTS

| | | | | |
|---|---|---|---|---|
| 584,999 | A | * | 6/1897 | Goldsmith ............. B43K 21/22 221/267 |
| 6,860,666 | B2 | | 3/2005 | Chien |
| 7,226,228 | B1 | * | 6/2007 | San Miguel ..... A61B 17/00491 401/57 |
| 7,320,553 | B1 | * | 1/2008 | Nunez ..................... B43K 1/12 401/10 |
| 8,932,295 | B1 | * | 1/2015 | Greenhalgh ....... A61B 17/1635 606/85 |

(Continued)

FOREIGN PATENT DOCUMENTS

GB 2355961 A 5/2001

OTHER PUBLICATIONS

PCT Search Report and Written Opinion dated Aug. 21, 2013, for PCT App No. PCT/CA2013/050396, filed May 24, 2013, titled Surgical Marker, Applicant: Dalhousie University.

*Primary Examiner* — David Walczak
(74) *Attorney, Agent, or Firm* — Polsinelli PC

(57) ABSTRACT

A marking instrument having a plurality of removable writing nibs serially aligned so that an operator can remove a spent or fluid-affected writing nib and, thereby, access a fresh writing tip.

9 Claims, 13 Drawing Sheets

(56) References Cited

U.S. PATENT DOCUMENTS

| | | | |
|---|---|---|---|
| 2001/0036383 A1* | 11/2001 | Cirlin | A45D 40/24 401/57 |
| 2003/0194260 A1* | 10/2003 | Ward | B43K 8/02 401/199 |
| 2006/0229652 A1 | 10/2006 | Lio et al. | |

* cited by examiner

SURGICAL MARKER

CROSS REFERENCE TO RELATED APPLICATIONS

This application is a continuation of Patent Cooperation Treaty Application Ser. No. PCT/CA2013/050396, filed May 24, 2013, which claims the benefit of U.S. Provisional Patent Application Ser. No. 61/651,451, filed May 24, 2012, both entitled "Surgical Marker," which are incorporated by reference herein in their entireties.

BACKGROUND

1. Technical Field

The present technology relates generally to a marking apparatus and more specifically to a marker for use during surgery.

2. Introduction

The use of marking devices during surgery is common. Indeed, many surgical procedures require planning out incisions in skin, or other tissues. For example, often a surgeon will mark lines on a patient's body so as to know the proper place and length of the incision or incisions which will be made during the operation. Such lines can be particularly important in specialties such as plastic surgery where the operation is being conducted for cosmetic reasons. In these cases, it is extremely important that the incisions be made at the proper locations, and of the appropriate lengths. However, this is often difficult to do during surgery without the aid of markings.

Typically, a surgeon will use a felt tip pen to mark lines representing the desired incisions. However, surgical markers having felt tips lose their ability to write when they come into contact with fluid. Therefore, when the fluids that are used on the patient's body prior to surgery or when body fluids are exposed during the surgery come into contact with a marker's tip, the fluid impedes the marker's ability to make effective markings. Also, when marking surfaces within a wound, i.e. bone exposed after making an incision, fluid is nearly always present and detrimental to the marker's ability to mark.

Surgeons prefer to use a marker that is easy to hold and write with. Unfortunately, as explained above, current disposable markers have an incredibly poor ability to write once their tip gets wet and, after each time a marker is rendered ineffective through fluid contact, surgeons do not want to have to sterilize a new marker or open another pre-sterilized marker package. Accordingly, some surgeons rely on primitive marking techniques.

SUMMARY

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by practice of the principles set forth herein.

To overcome the problem of fluid-affected tips of known surgical markers, an improved surgical marker is disclosed herein that allows a user to remove fluid-affected tips from a marker body and expose a new, fresh tip. Some embodiments of the present technology involve a marking instrument having a plurality of removable writing nibs serially aligned so that an operator can remove a spent or fluid-affected writing nib and, thereby, access a fresh writing tip. In some embodiments, the writing nibs are comprised of a substantially rigid nib base and a fluid-filled writing tip.

The nibs and writing tips can take various forms and configurations based on the mechanism used to advance new nibs and based on a requirement specific to the surgical application. For example, in various embodiments, the writing tips can be configured with a fine-tip, wide-tip, chisel-tip, etc. In some embodiments, the tips contain a xylene-based ink used in permanent markers. In some embodiments, the tips contain crystal violet ink such as Gentian violet ink having antibacterial, antifungal, and anthelmintic properties.

In some embodiments of the present technology each of the nibs can contain a radiopaque element that is detectable in the presence of X-Ray radiation, such as radiopaque thread. Also, in some embodiments, each of the nibs is labeled with a number and a manifest is printed on or packaged with the surgical marker, wherein the manifest lists the nib numbers so a surgeon or attending nurse can account for each nib post surgery.

Some embodiments of the present technology involve a marker housing containing the plurality of removable nibs having writing tips and a mechanism for advancing a new, serially located nib into a writing position. In some embodiments, the mechanism involves an outer housing, a spring-loaded inner housing, and an advancement mechanism for pushing serially positioned writing nibs into a writing position after removal of a spent or fluid-affected writing nib.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof, which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure.

The present disclosure addresses the need in the art for a surgical marker that provides a medical professional the chance to switch out ink-filled nibs upon an ink tip coming into contact with fluid or otherwise being rendered useless.

Some embodiments of the present technology involve a marking instrument having a plurality of removable writing nibs serially aligned so that an operator can remove a spent or fluid-affected writing nib and, thereby, access a fresh writing tip.

Some embodiments of the present technology involve a surgical marker containing a plurality of removable nibs having writing tips and an ejection mechanism for removing a nib and advancing a new, serially located nib into an exposed writing position when the writing tip of previously exposed nib is removed from the housing, e.g. after being exposed to fluid that rendered the previously exposed writing tip less useful or useless to make markings.

The nibs and writing tips can take various forms and configurations based on the mechanism used to advance new nibs and based on a requirement specific to the surgical application. For example, in various embodiments, the writing tips can be configured with a fine-tip, wide-tip, chisel-tip, etc. In some embodiments, the tips contain a xylene-based ink used in permanent markers. In some embodiments, the tips contain crystal violet ink such as Gentian violet ink having antibacterial, antifungal, and anthelmintic properties.

The removable writing nibs can be small and, therefore, easy to misplace in an operative field. Accordingly, in some embodiments of the present technology each of the nibs can contain a radiopaque element that is detectable in the presence of X-Ray radiation, such as radiopaque thread. Likewise, in some embodiments, each of the nibs is labeled with a number and a manifest is printed on or packaged with the surgical marker, wherein the manifest lists the nib numbers so a surgeon or attending nurse can account for each nib post surgery.

Some embodiments of the present technology involve a surgical marker having an outer housing and an inner housing containing a plurality of removable writing nibs and containing a mechanism for advancing the writing tip of a new, serially located nib into a writing position when a previously-exposed nib is removed from the housing.

Figure 1:
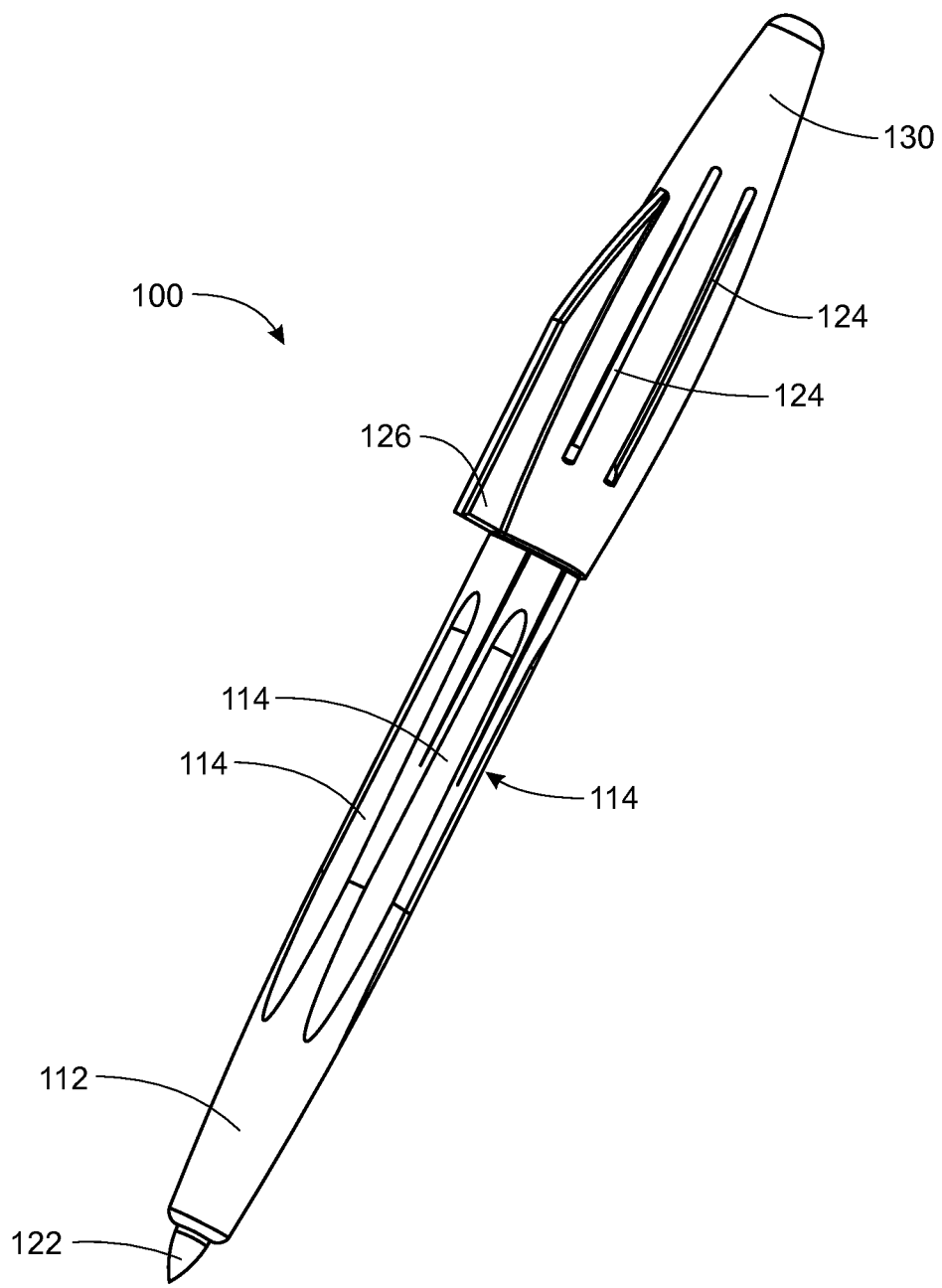
FIG. 1 illustrates an outer housing of a surgical marker according to some embodiments of the present technology.

FIG. 1 illustrates a surgical marker 100 with an outer housing 112, an end cap 130 sealing the distal end of the outer housing, and a writing tip 122 protruding from an opening at the proximal end of the outer housing 112 according to some embodiments of the present technology. In some embodiments, the end cap 130 and the writing tip 122 are part of an inner housing assembly, as explained below.

The outer housing 112 can include one or more grooves, ridges, depressions, bumps, etc. configured to provide a better grip on the marker 100, especially in the presence of fluid. As shown in FIG. 1, the outer housing 112 of the surgical marker 100 includes a plurality of grooves 114 for providing grip to the outer housing 112 and the end cap 130 has grooves 124 and ridge 126 to provide grip and to facilitate rotation of the end cap 130.

Figure 2A:
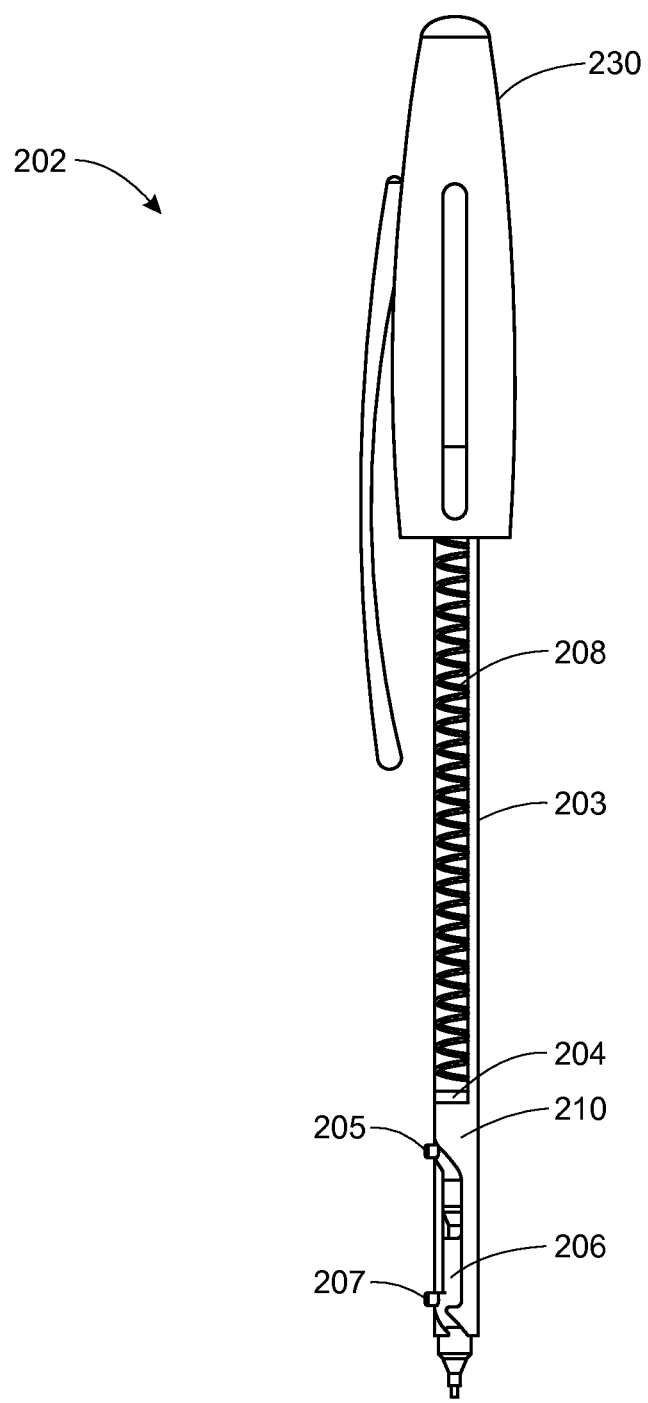
FIG. 2A illustrates an inner housing assembly of a surgical marker according to some embodiments of the present technology.
Figure 2B:
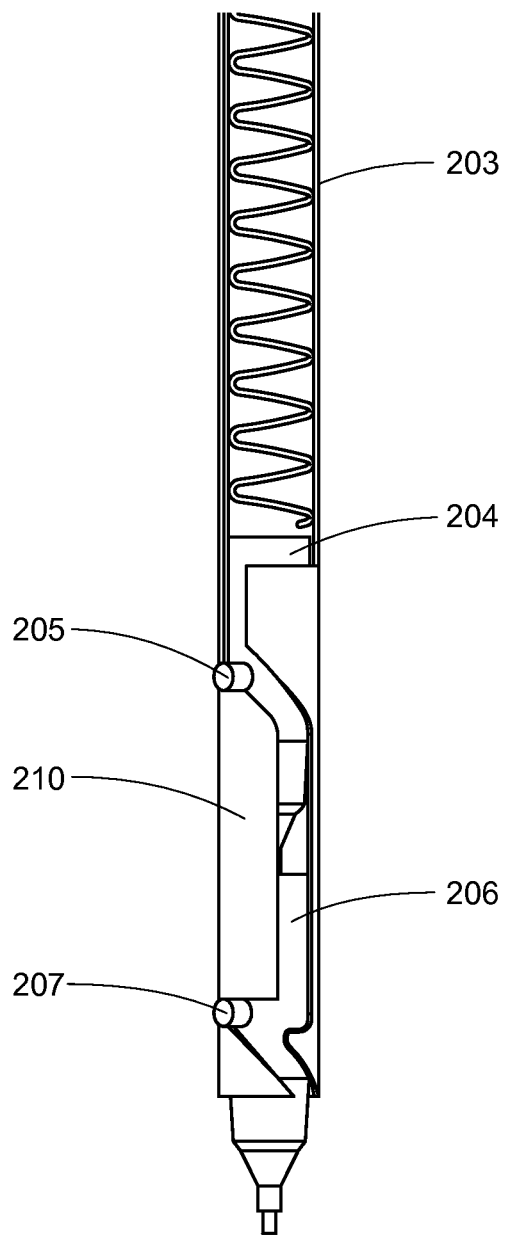
FIG. 2B illustrates a more-detailed view of the inner housing assembly of a surgical markers according to some embodiments of the present technology.

FIG. 2A illustrates an inner housing assembly 202 containing serially positioned removable nibs 204, 206 within a substantially cylindrical inner housing 203, a spring 208 for providing a force on the nibs 204, 206, and an engagement mechanism 210 for allowing the nibs 204, 206 to be alternatively engaged in a writing position and in an ejection/advancement position (explained in greater detail below). The nibs 204, 206 are configured with projections 205, 207 extending from the nibs in a direction substantially orthogonal to an axis parallel to the length of the inner housing 203. The projections 205, 207 engage with the engagement mechanism as explained below. FIG. 2B illustrates a more-detailed view of the engagement mechanism 210 according to some embodiments of the present technology.

The inner housing assembly 202 also includes an end cap 230 mechanically coupled with the inner housing 203 such that rotation of the end cap 230 about an axis parallel to the length of the inner housing 203 causes the inner housing 203 to rotation in the same direction.

In some embodiments of the present technology, a channel is disposed in an inner surface of the outer housing of a surgical marker and the channel is configured to maintain alignment of the projections on the nibs contained in an inner housing such that rotation of the inner housing causes the engagement mechanism to rotate relative to the position of the projections.

Figure 3:
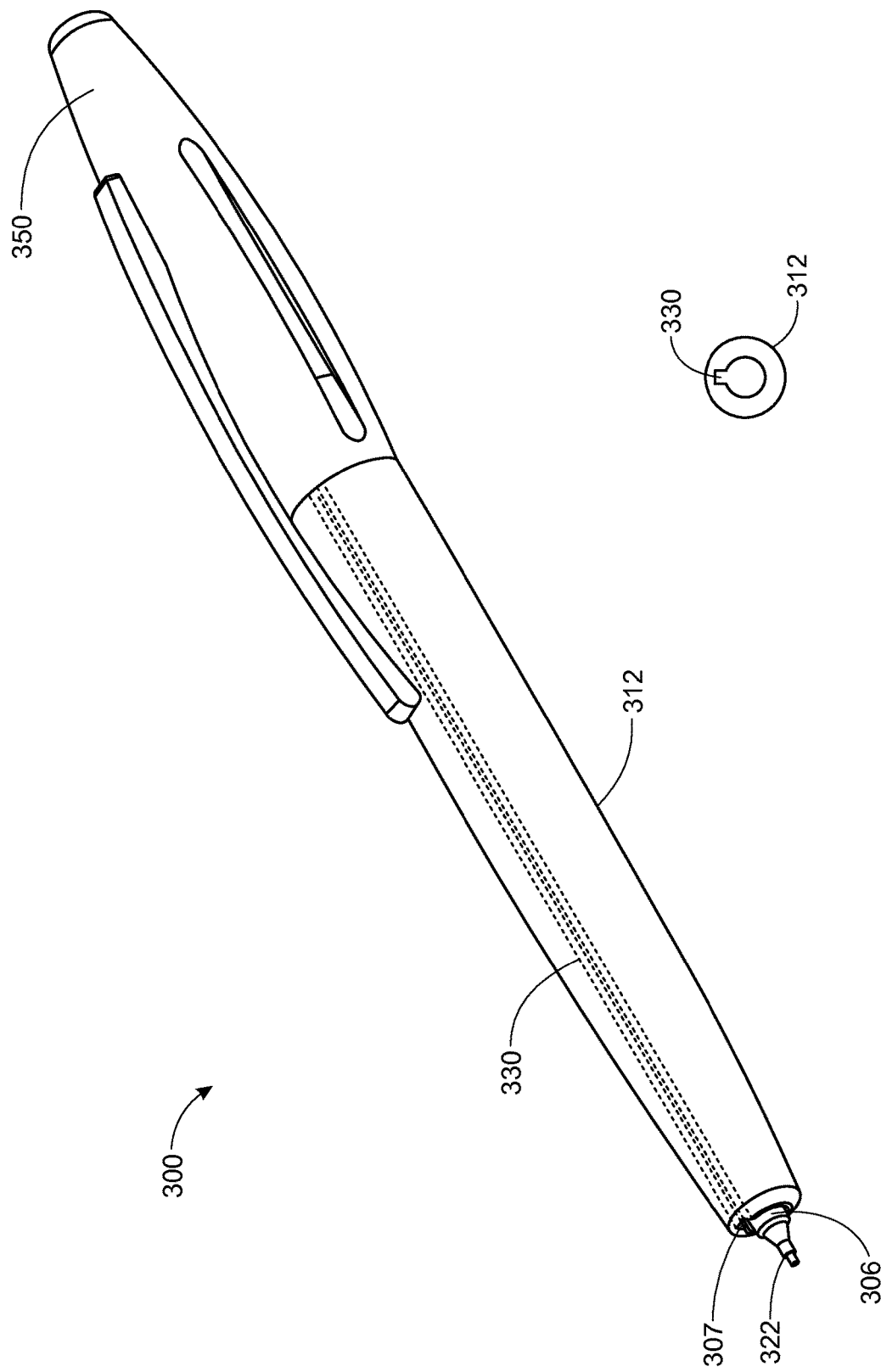
FIG. 3 illustrates a surgical marker with an outer housing having a channel disposed in its inner surface according to some embodiments of the present technology.

FIG. 3 illustrates a surgical marker 300 with an outer housing 312 having a channel 330 disposed in its inner surface according to some embodiments of the present technology. The surgical marker 300 also includes an end cap 350 and a nib 306 having writing tip 322 protruding from an opening at the proximal end of the outer housing 312. The nib 306 also includes a projection 307 disposed in the channel 330 such that a rotation of the end cap 350 causes rotation of the inner housing (not shown) and the engagement mechanism (not shown), but not nib 306 or the other sequentially aligned nibs (not shown).

Figure 4A:
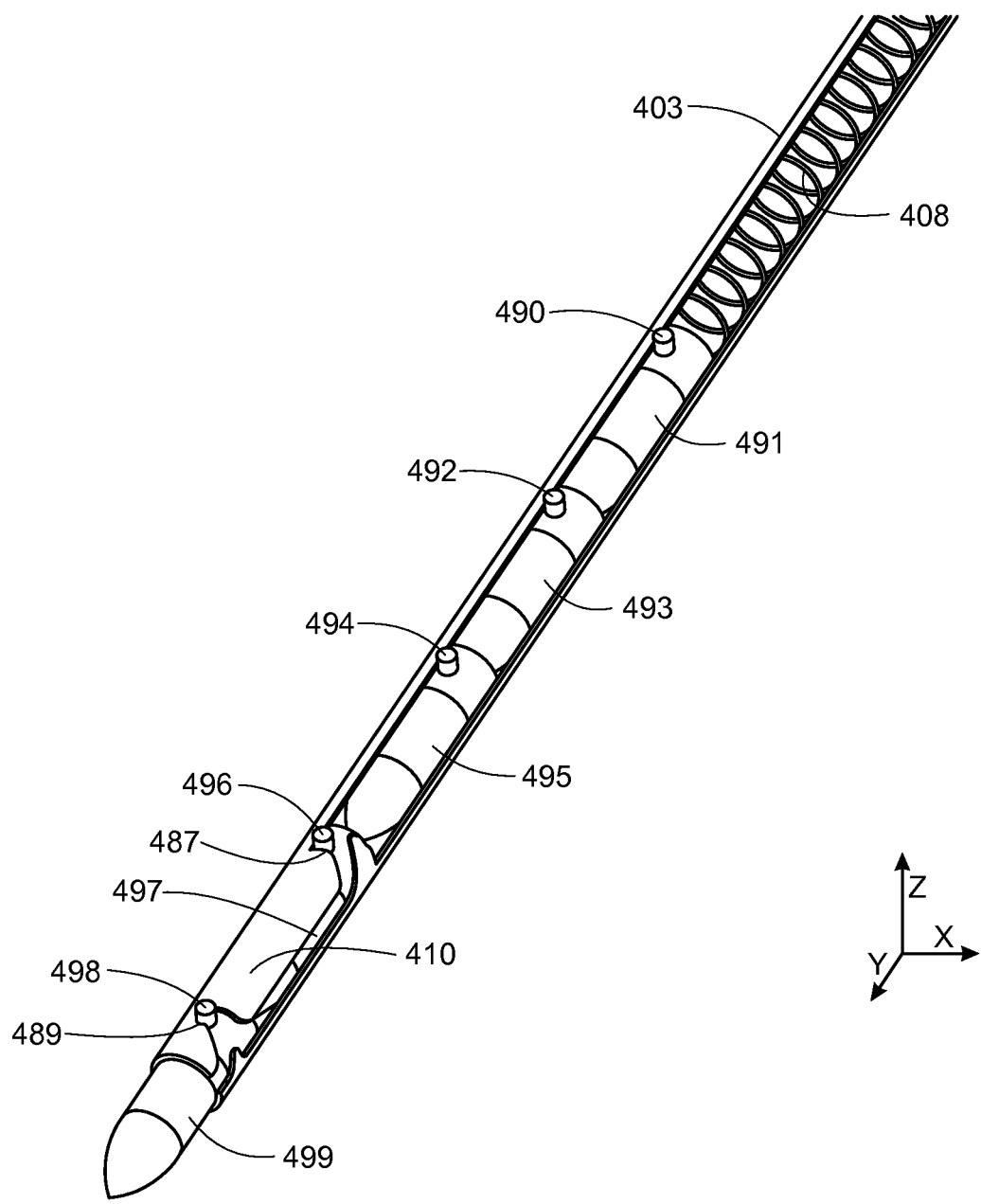
FIG. 4A illustrates an engagement mechanism in a first position according to some embodiments of the present technology.

FIG. 4A illustrates an engagement mechanism 410 before a rotation of an inner housing 403 of a surgical marker with a plurality of nibs 499, 497, 495, 493, 491 having projections 498, 496, 494, 492, 490 configured in a channel disposed in the inner surface of an outer housing (not shown) according to some embodiments of the present technology. Due to their configuration in the channel, the projections 498, 496, 494, 492, 490 resist the rotation of the inner housing, thereby allowing the engagement mechanism to move relative to the nibs 499, 497, 495, 493, 491.

The engagement mechanism 410 also includes a plurality of channels and flanges for alternatively resisting and allowing a force of the spring 408 to impart motion to the nibs 499, 497, 495, 493, 491 depending on the position of the aligned nibs within the engagement mechanism. As shown in FIG. 4A, flanges 489 and 487 contact projections 498 and 496 and resist motion of the nibs 499, 497, 495, 493, 491 in the y-direction.

Figure 4B:
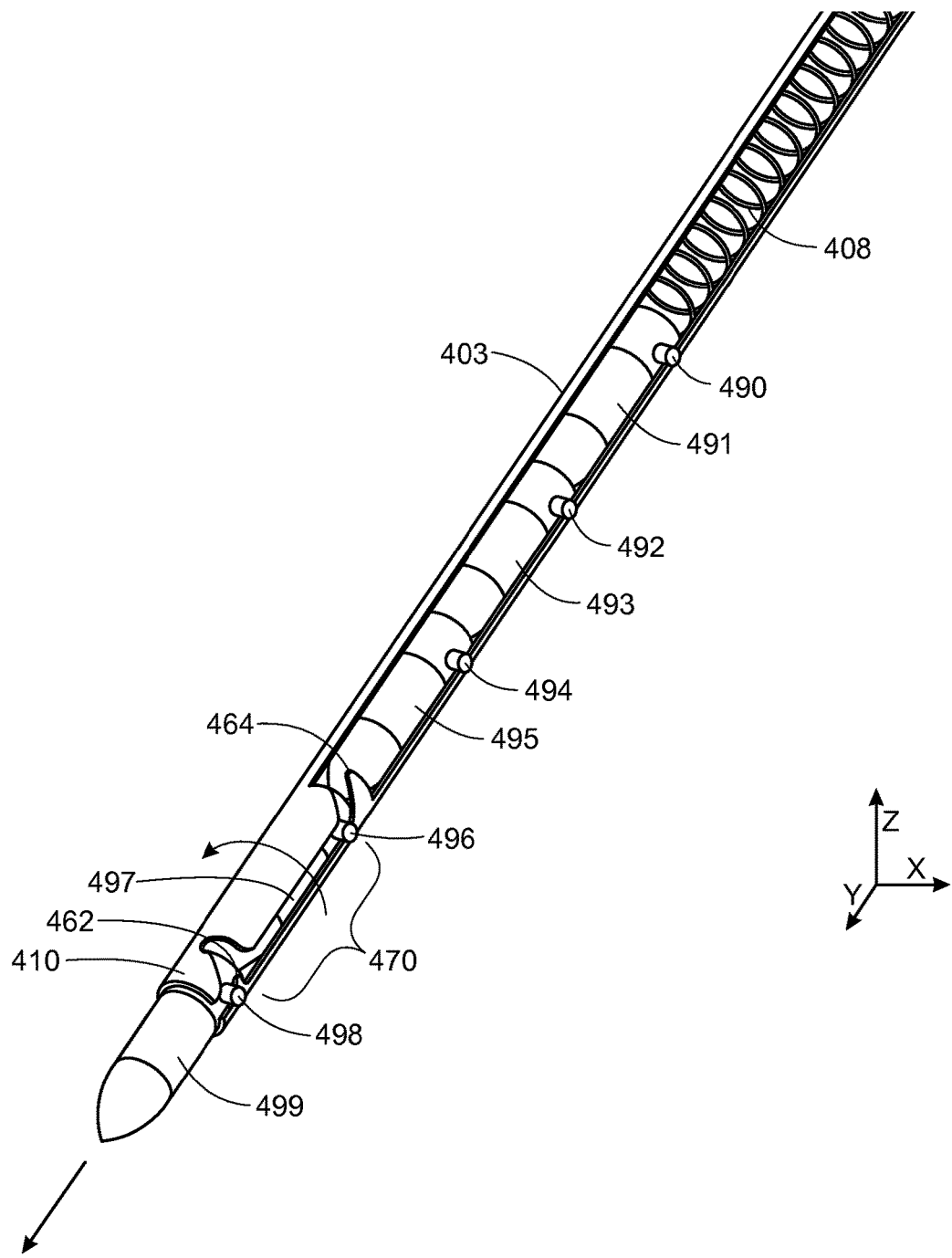
FIG. 4B illustrates an engagement mechanism in a second position according to some embodiments of the present technology.

FIG. 4B illustrates the engagement mechanism 410 after a rotation of an inner housing 403 according to some embodiments of the present technology. According to FIG. 4B, nothings resists the force imparted on the nibs 499, 497, 495, 493, 491 and the nibs 497, 495, 493, 491 move through a channel 470 while the nib 499 can be removed. The engagement mechanism 410 also includes flanges 462, 464 for stopping motion of the remaining nibs 497, 495, 493, 491. Accordingly, the inner housing 403 can be rotated in the opposite direction and back into the position shown in FIG. 4A with the flanges 489 and 487 locking the linear motion of the remaining nibs 497, 495, 493, 491 once again.

Figure 5A:
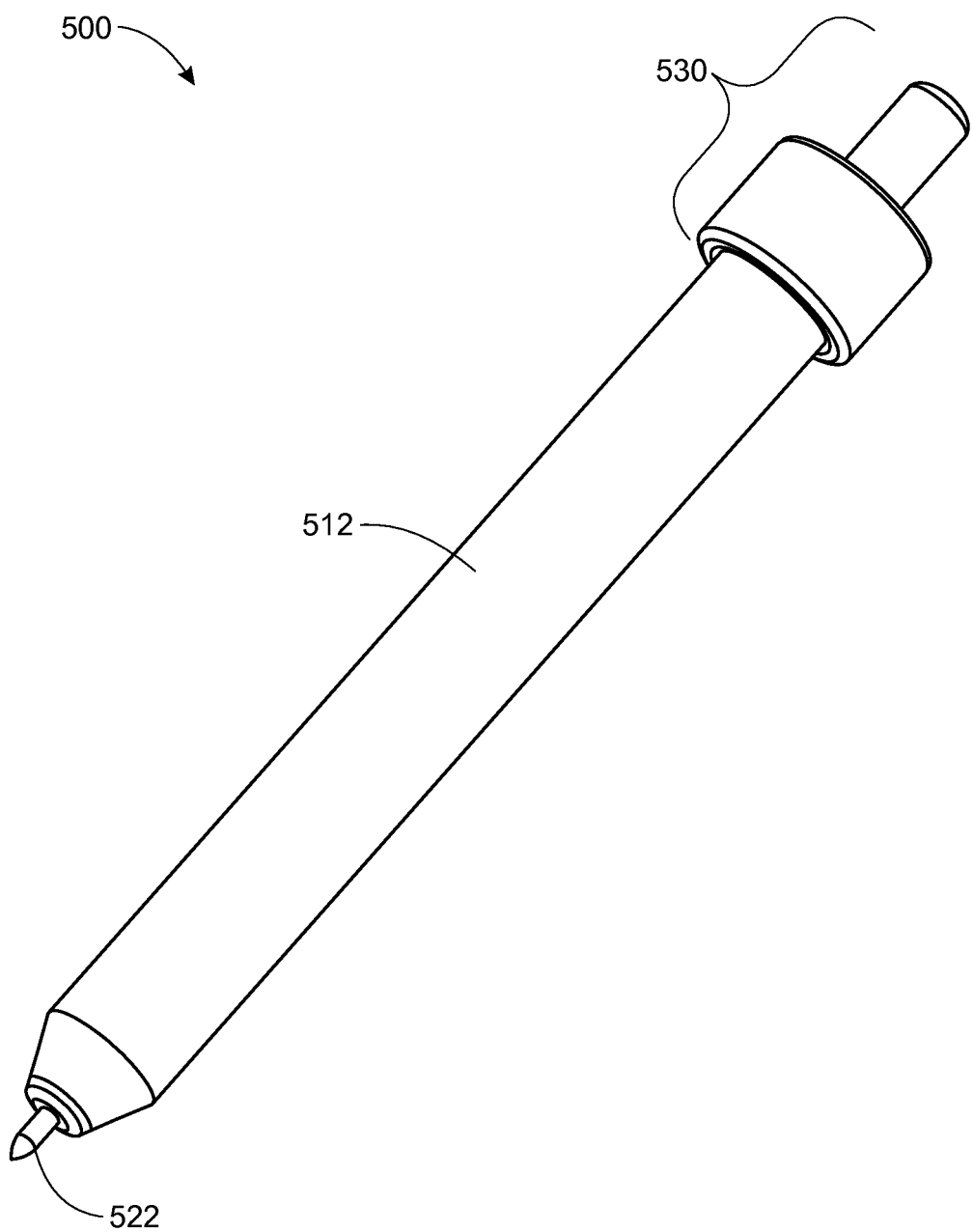
FIG. 5A illustrates a surgical marker with a push-button interface according to some embodiments of the present technology.
Figure 5B:
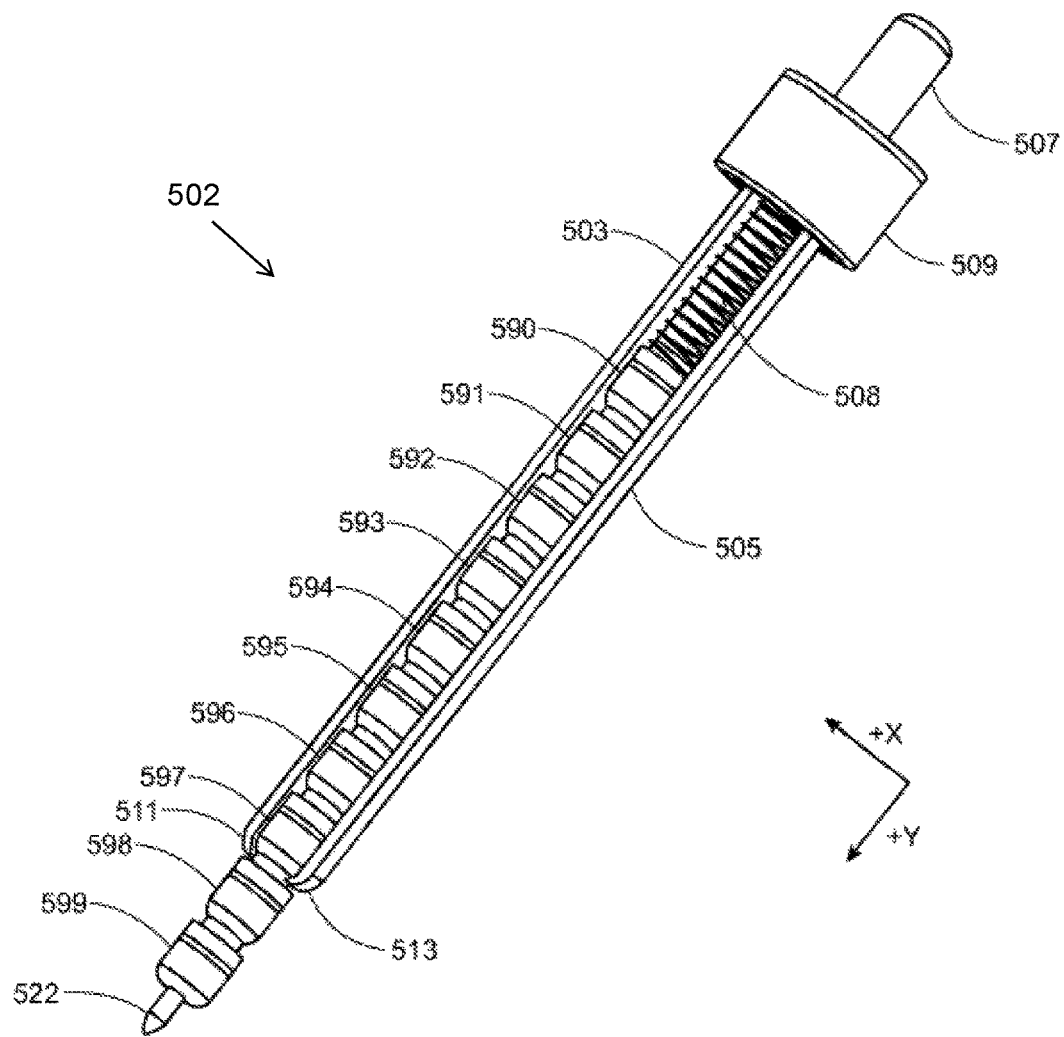
FIG. 5B illustrates a surgical marker having an inner housing assembly containing serially positioned removable nibs housed between two at-least-partially resilient axial arms according to some embodiments of the present technology.
Figure 5C:
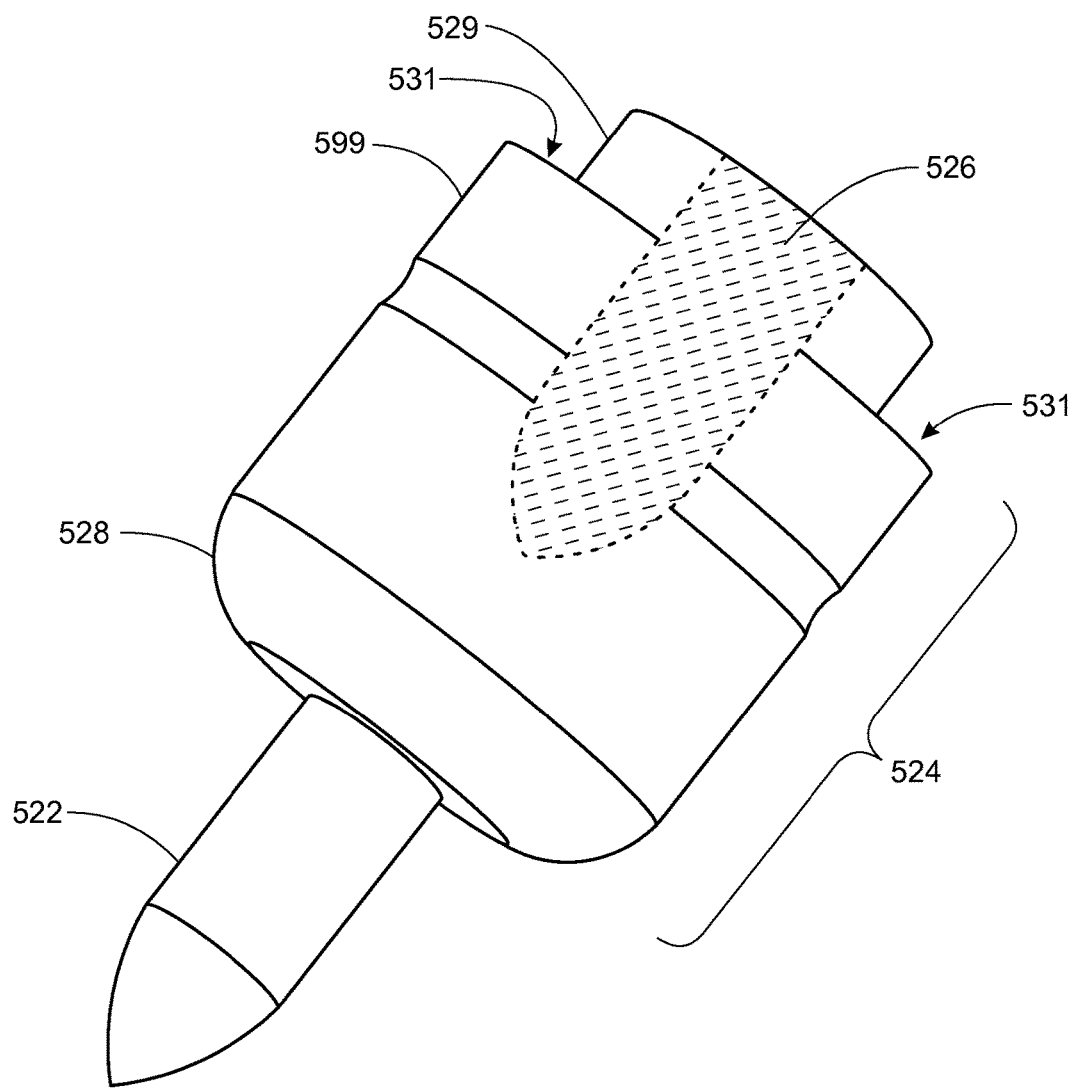
FIG. 5C illustrates a close up view of a removable nib according to some embodiments of the present technology.

FIGS. 5A-5C illustrate an exemplary implementation of a surgical marker having an outer housing and an inner housing containing a plurality of removable writing nibs and containing a mechanism for advancing the writing tip of a new, serially located nib into a writing position when a previously-exposed nib is removed from the housing.

FIG. 5A illustrates a surgical marker 500 with an outer housing 512, an end cap assembly 530 sealing the distal end of the outer housing, and a writing tip 522 protruding from an opening at the proximal end of the outer housing 512 according to some embodiments of the present technology. In some embodiments, the end cap 530 and the writing tip 522 are part of an inner housing assembly, as explained below.

FIG. 5B illustrates an inner housing assembly 502 containing serially positioned removable nibs 599, 598, 597, 596, 595, 594, 593, 592, 591, 590 housed between two at-least-partially resilient axial arms 503, 505. The axial arms 503, 505 are mechanically coupled with a push-button interface 507 through an interface in an outer housing end cap 509. The interface in the outer housing end cap allows the push-button interface 507 to traverse a distance in the y-direction, thereby moving the axial arms 503, 505 toward the front most removable nib. Additionally, a spring 508 is positioned between the axial arms 503, 505 and can serve the purpose of: resisting the depression of the push-button interface in order to return to the push button interface back to a starting position; and applying a force on the serially positioned removable nibs 599, 598, 597, 596, 595, 594, 593, 592, 591, 590 when the axial arms are moved away from one another (as explained below) thereby allowing advancement of a sequential nibs FIG. 5C illustrates a close up view of removable nib 599 according to some embodiments of the present technology. The removable nib 599 can comprise a substantially rigid body portion 524, a writing tip 522, and a cavity (indicated by dashed lines) 526. The cavity 526 is configured to accommodate the writing tip of a sequentially positioned nib in a nested manner. Nesting sequentially positioned nibs can seal writing tips requiring a substantially hermetic seal to avoid becoming dried out in the present of atmosphere. The removable nib 599 also includes: an angled flange 528 on the edge of the substantially rigid portion 524 closest to the writing tip 522; and a valley terminal portion 529 that defines a ledge 531.

Referring again to FIG. 5B, the terminal end of the axial arms 503, 505 include inward grips 511, 513 that are configured inward in an angle similar to the angle of the angled flange 528 of FIG. 5C. In operation, upon the depression of the push-button interface 507 in the positive y-direction is resisted by the end cap 509 and causes the axial arms 503, 505 to push removable nib 599 out of the outer housing 512 and removable nib 598 into the position previously occupied by removable nib 599. The spring 508 resists the depression of the push-button interface 507; and, upon the depressing force being removed, the spring 508 causes the push-button interface 507 and the axial arms 503, 505 to move in the minus y-direction. As explained above, the axial arms 503, 505 are at least partially resilient. Accordingly, the motion of the axial arms 503, 505 caused by the resistance force of the spring 508 can cause the inward grips 511, 513 to push against the surface of the angled flange 528 of nib 597 causing the axial arms 503, 505 to become temporarily displaced in the positive x-direction and negative x-direction, respectively. Once the axial arms 503, 505 are displaced away from one another, the spring 508 serves its second purpose of advancing the nibs 597, 596, 595, 594, 593, 592, 591, 590 in the positive y-direction. Once the nib 597 advances far enough for the inward grips to traverse the threshold of the valley terminal portion 529, the spring-force initiated geometric force causing displacement of the axial arms 503, 505 is terminated and the inward grips 511, 513 snap back onto the valley terminal portion 529. Additionally, a subsequent writing force applied in the negative y-direction (through a writing pressure) is resisted by the ledge 531 contacting the inward grips 511, 513.

In some embodiments, the push-button interface 507 and the outer housing end cap 509 are configured with a locking mechanism (not shown) which causes a rotation of the push-button interface 507 about the y-axis to lock out depression of the push-button interface.

FIGS. 6A-6F illustrate an exemplary implementation of a surgical marker having an outer housing containing a plurality of removable writing nibs and containing a rotation mechanism for advancing the writing tip of a new, serially located nib into a writing position when a previously-exposed nib is removed from the housing.

Figure 6A:
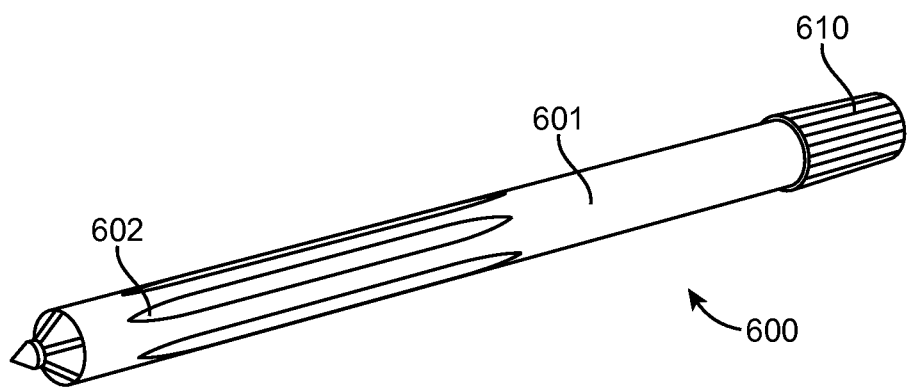
FIG. 6A illustrates a surgical marker with a knob-actuated nib-advancement according to some embodiments of the present technology.

FIG. 6A illustrates a surgical marker 600 with an outer housing 601, a knob 610 covering the distal end of the outer housing and attached to a knob assembly (not shown in FIG. 6A), a nib retainer 620, and a writing tip 630 or 640 protruding from an opening at the proximal end of the outer housing 601 according to some embodiments of the present technology. The outer housing may contain features, such as grooves 602, indentations, protruding bumps, or edges, that increase the ability of the surgical marker to be gripped by a gloved hand, specifically when liquid or bodily fluid is present. An example of grooves 602 is represented in FIG. 6A.

Figure 6B:
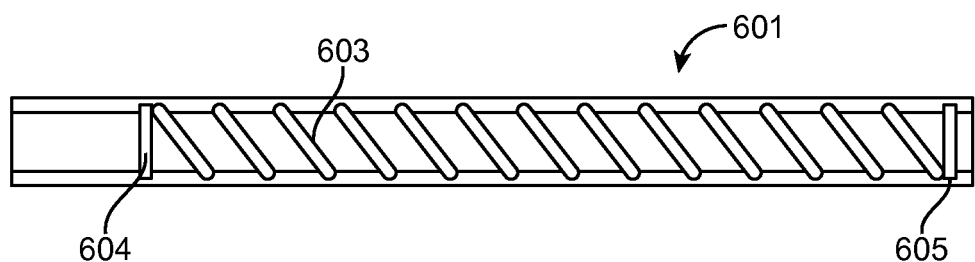
FIG. 6B illustrates an outer housing of a surgical marker containing internal screw threads according to some embodiments of the present technology.

FIG. 6B illustrates a cross-sectional view of an outer housing 601. The outer housing is generally spherical in shape, but may have features on the outer surface as described in the preceding paragraph. The inside of the outer housing is hollow, containing a through hole along the longitudinal axis, which may have one or more diameters. Most of the through hole contains internal threads 603 that convert rotation of the knob, inner housing, and nibs into translation of the nibs along the longitudinal axis. The internal threads 603 are sized with a pitch such that a small number of revolutions of the knob result in enough axial translation to cause ejection of a nib. In some embodiments, a single nib ejection may occur between 0.5 and 4 revolutions of the knob, depending on sizing of the various components. It is further noted that the screw thread pitch will be sized such that pressure on the tip from normal use does not cause the tips to recede with in the outer housing.

The outer housing 601 also contains two engagement features. One engagement feature 604 is sized and configured to retain the nib retainer 620. This engagement feature 604 is located on the distal end of the outer housing 601. In some embodiments, this nib retainer engagement feature 604 is in the form of an internal radial groove with a diameter greater than the base diameter of the outer housing through hole. The second engagement feature 605 is at the proximal end of the outer housing 601. This engagement feature 605 is sized and configured to retain the knob 610 and associated assembly. In some embodiments, this knob assembly engagement feature 605 is in the form of an internal radial groove with a diameter greater than the base diameter of the outer housing through hole. While the screw thread 603 is only shown in FIG. 6B to be located between the engagement features 604 and 605, it may extend farther and may be present along the entire length of the outer housing.

Figure 6C:
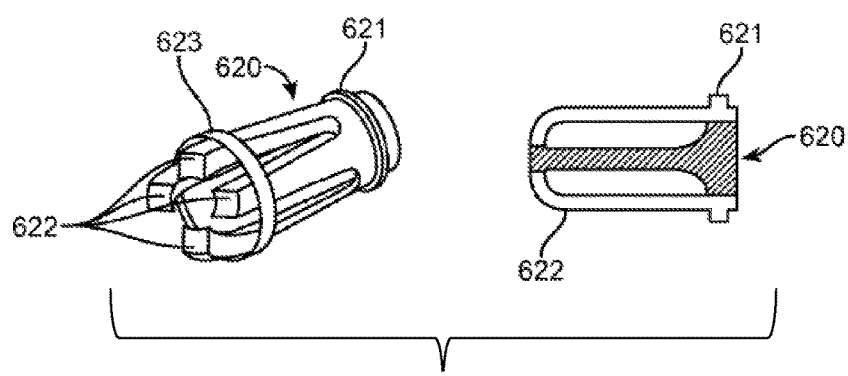
FIG. 6C illustrates a nib retention mechanism of a surgical marker according to some embodiments of the present technology.

FIG. 6C illustrates, via a graphical projection and cross sectional view, a nib retainer 620 that is configured to retain one or more nibs in series, while allowing the marker tip of the nib to protrude distally from the nib retainer 620 (shown in FIG. 6A). The nib retainer contains a proximal and a distal end and may be in a cylindrical-like shape. The nib retainer 620 contains a through hole that is sized and configured to retain a nib 630 or 640. The nib retainer 620 contains an engagement feature 621 that allows the nib retainer 620 to engage with the complementary engagement feature 604 of the outer housing 601. In some embodiments, the engagement feature 621 on the nib retainer is in the form of a protruding ring near the proximal end of the nib retainer 620, as illustrated in FIG. 6C.

The nib retainer 620 also contains a feature to temporarily hold one or more nibs in series. In some embodiments, this retention feature is in the form of flexible or bendable arms that can expand from a closed position to an open position to enlarge the distal opening and allow a nib to be ejected from the distal end. FIG. 6C illustrates four of these arms. In some embodiments, an elastic-like feature 623 may be present to assist the flexible arms in returning to their closed position. When expanded, this feature 623 provides a radial force to move the flexible arms back to the closed position, such that the subsequent serial nib can be retained.

Figure 6D:
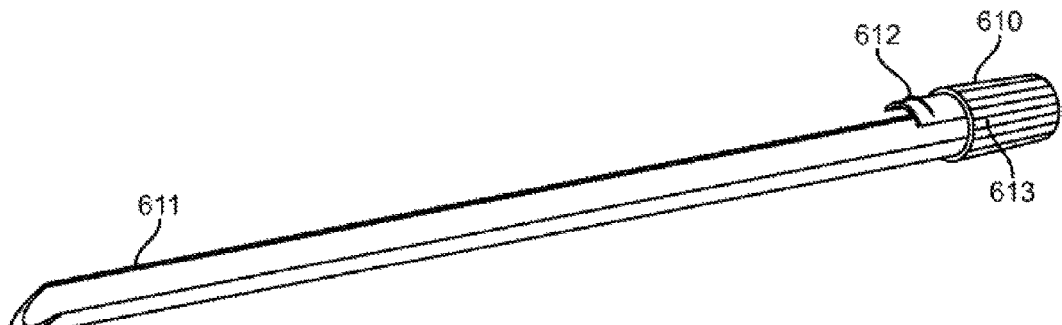
FIG. 6D illustrates an inner housing of a surgical marker according to some embodiments of the present technology.

FIG. 6D illustrates a graphical projection of the knob assembly. The knob assembly contains three components: knob 610, nib rotation support 611, and knob support 612. The knob 610 is generally cylindrically shaped and is located on the proximal end of the knob assembly. In some embodiments, the knob 610 has features to increase the ability to be gripped with gloved fingers. These grip features can take the form of edges 613 (as illustrated in FIG. 6D), raised ridges, indentations/troughs, or other similar features that would be obvious to one of ordinary skill in the art. The knob 610 is coupled to the nib rotation support 611 and to the knob support 612. In some embodiments, the knob 610 is hollow and the nib rotation support 611 and knob support 612 are coupled to the knob 610 within this hollow feature.

In some embodiments, the proximal end of the knob is closed, while, in other embodiments, the proximal end of the knob is open.

The nib rotation support 611 is sized and configured such that it can be inserted into the through hole of the outer housing and is able to support the series of axially aligned nibs. In some embodiments, the nib rotation support 611 is in the form of a hollow cylinder that is partially open along an area parallel to the longitudinal axis. In other embodiments, the nib rotation support 611 is in the form of a cylinder with a cylindrical groove placed in the longitudinal surface. Both embodiments result in a non-continuous hollow cylinder, where two defined interface sides are parallel to the cylindrical axis and run the length of the nib rotation support.

The knob support 612 contains a knob engagement feature that retains the knob and knob assembly to the outer housing. When the knob assembly is inserted into the outer housing 601, the knob engagement feature of the knob assembly complementarily engages with the knob engagement feature of the outer housing 605, joining the components. These complementary engagement features prevent relative axial displacement between the knob assembly and outer housing, but permit rotational movement. In some embodiments, the knob engagement feature on the knob support 612 is in the form of a raised axial protrusion, as shown in FIG. 6D.

While the knob assembly is described as multiple parts that are connected together, the knob assembly may be a single continuous component in some embodiments.

Figure 6E:
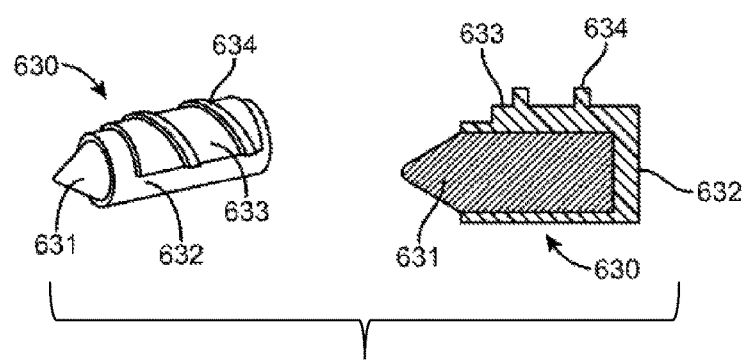
FIG. 6E illustrates a base traveler nib of a surgical marker according to some embodiments of the present technology.

FIG. 6E illustrates, via a graphical projection and cross sectional view, a traveler nib 630. This traveler nib 630 is sized and configured to fit within the through hole of the outer housing 601 while being supported by the nib rotation support 611. The traveler nib is composed of a marker tip 631 and traveler nib housing 632. The marker tip 631 contains the marker ink, fluid, paint, or similar and is connected to the traveler nib housing 632. In some embodiments, the marker tip 631 is in the shape of a cylinder with a pointed dip on the distal end. The traveler nib housing is in the basic shape of a cylinder with one or more external partial screw threads 634 that interface with the internal screw threads 603 of outer housing 601. The traveler nib housing 632 has a closed distal end to prevent the marker tip from drying out. The external partial screw threads 634 are located on a raised radial projection 633, which create a rotational interface in the form of defined edges generally parallel to the axis of the traveler nib housing 632. The rotational interface of the radial projection 633 contacts the interface sides of nib rotation support 611 when the traveler nib is positioned within the nib rotation support 611. When the knob assembly is rotated, the contact between the edges of the nib rotation support 611 and radial projection 633 cause the traveler nib to rotate with the same rotational displacement. When the traveler nib 630 is placed within the nib rotation support 611 and both are placed within the outer assembly, when the outer assembly is held stationary and the knob is rotated, it causes the traveler nib to revolve and translate axially, due to the engaged screw thread.

Figure 6F:
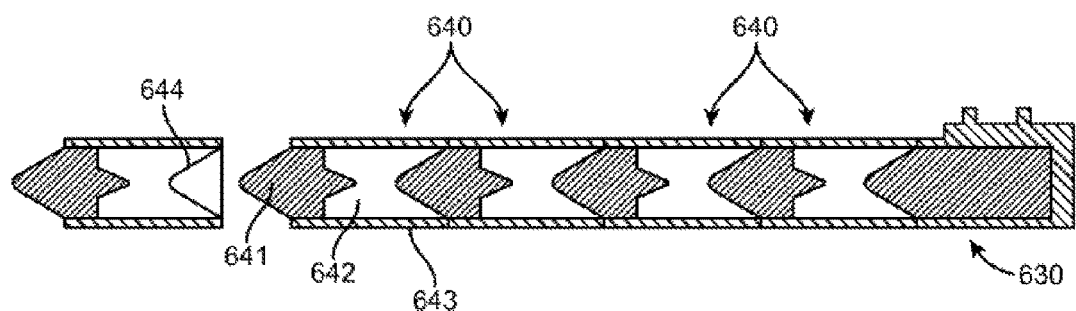
FIG. 6F illustrates nested nibs of a surgical marker according to some embodiments of the present technology.

FIG. 6F illustrates, via a cross-sectional view, a series of standard nibs 640 and a traveler nib 630. The standard nibs 640 are similar to the traveler nib 630. The standard nibs contain a marker tip 641 that contains marker ink, fluid, paint, or similar and is connected to the standard nib housing 643. In some embodiments, the standard nib also contains a material or wadding 642 proximal to the marker tip 641 and contained within the standard nib housing 643. This wadding 642 may hold a supply of marker fluid (or similar) and may help prevent the marker tip from drying out. The nibs are nested together axially, with the marker tip of one nib complementarily nesting into the more distal nib via an indentation feature 644. Each standard nib 640 is sized and configured to have the marker tip nest in the more distal nib, resulting in the nib housings forming a continuous or nearly continuous housing, reducing the evaporation and drying out of the marker fluid present in the nibs. A traveler nib 630 is positioned as the most proximal nib and it is utilized to drive and eject the other nibs, allowing a fresh marker surface to be utilized.

When fully assembled, as the knob 610 is rotated, the nib rotation support 611 is also rotated. The edges of the nib rotation support contact the raised radial projection of the traveler nib causing it to rotate. The external threads on the traveler nib follow the internal threads on the outer housing, causing the rotation of the traveler nib to result in axial displacement. The axial displacement of the traveler nib results in axial displacement of the more distal standard nibs via the force imparted from the outer housing of one nib to the outer housing of the adjacent nib. The distal-most nib transfers to the force to the nib retainer 620. The force causes the engagement feature 604 of the nib retainer to expand, resulting in ejection of the distal-most nib. In some embodiments, once a portion of the nib housing extends distal to the nib retainer, the exposed nib may be removed by hand by pulling the nib distally.

The materials of the marker assembly may be varied and may consist of metallic, polymeric, and/or fibrous materials. In some embodiments, the materials may be selected at least partially based on their ability to be sterilized. In some embodiments, the housings of the standard and traveler nibs may be made from a radiopaque material, so they are visible on an x-ray scan. In some embodiments, the outer housings may be numbered or serialized via markings visible to the user.

Figure 7:
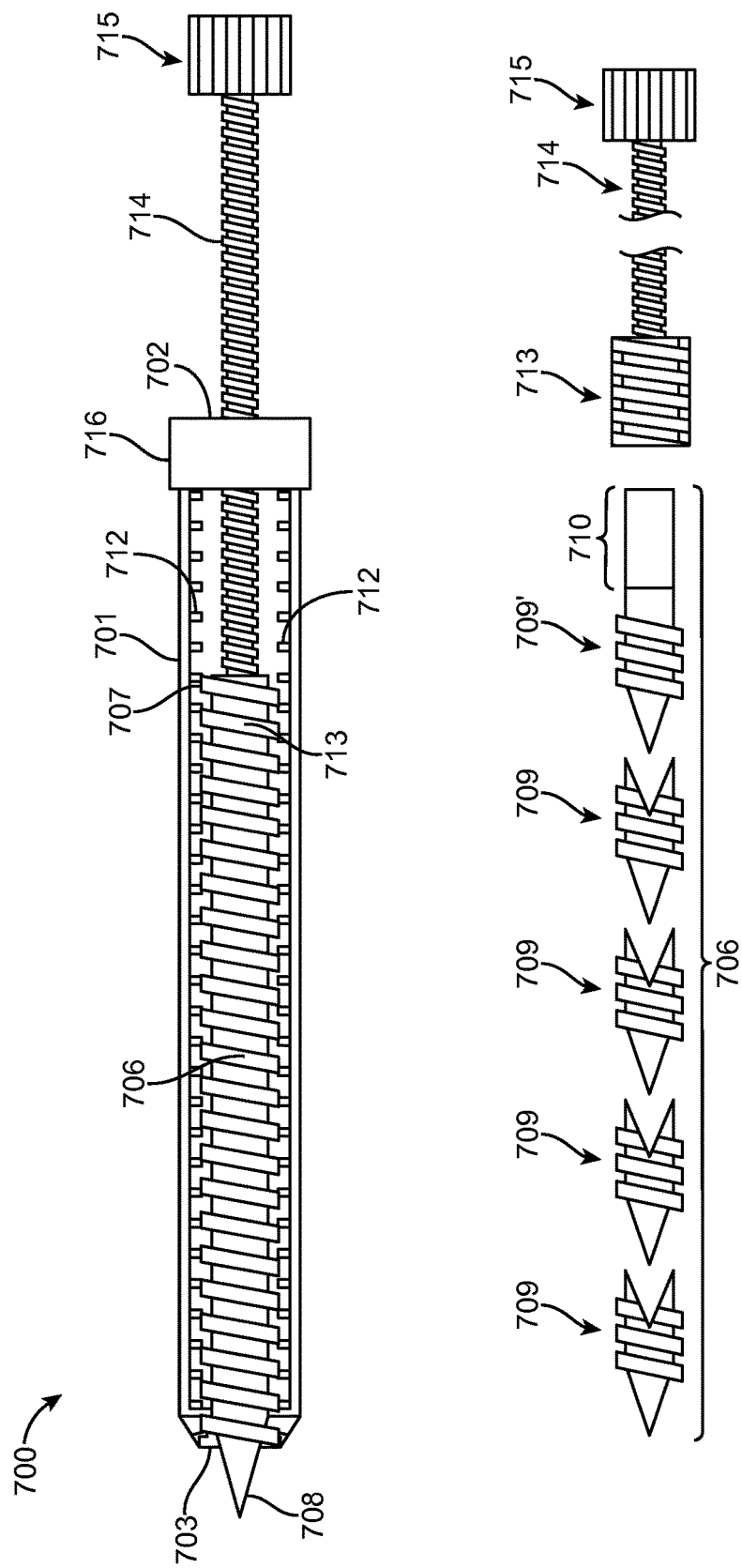
FIG. 7 illustrates a surgical marker with a knob-actuated nib-advancement according to some embodiments of the present technology.

FIG. 7 illustrates another embodiment of a surgical marker 700 according to some embodiments of the present technology. According to FIG. 7, the surgical marker 700 comprises a hollow body 701 with a proximal end 702 and a distal end 703. In some embodiments, the proximal end 702 is coupled to a cap 716 that has a through hole in the center.

The body 701 of the surgical marker 700 also contains a wadding 706 having a terminal end 707 and a tip 708 that extends through the distal end 703 of the body 701. The wadding 706 is coupled to a piston 713 which is subsequently coupled to a shaft 714 which is subsequently coupled to a knob 715. The piston 713 is located inside of the body 701. The shaft 714 is substantially parallel to the axis of the body and passes from the inside of the body through an opening on the distal end 703 to the outside of the body. In some embodiments, the shaft also passes through the opening in cap 716.

The marker 700 contains at least one pair of internal and external threads that form an advancement mechanism.

In some embodiments of the advancement mechanism, the cap 716 contains internal threads in the through hole and shaft 714 contains external threads. When the knob 715 is revolved and the body 701 is held stationary, the threads on the shaft 714 engage with the threads on the cap 716. The screw thread converts the rotational displacement into axial displacement of the knob, shaft, piston, and wadding, which are all coupled together. The wadding 706 is forced out the distal opening of the body 701.

In some embodiments of the advancement mechanism, the piston 713 contains external threads that engage with internal threads located on the inside of body 701. When the knob 715 is revolved and the body 701 is held stationary, the threads on the piston 713 engage with the threads on the body 701. The screw thread converts the rotational displacement into axial displacement of the knob, shaft, piston, and wadding, which are all coupled together. The wadding 706 is forced out the distal opening of the body 701.

In some embodiments of the advancement mechanism, the wadding 706 contains external threads that engage with internal threads located on the inside of body 701. When the knob 715 is revolved and the body 701 is held stationary, the threads on the wadding 706 engage with the threads on the body 701. The screw thread converts the rotational displacement into axial displacement of the knob, shaft, piston, and wadding, which are all coupled together. The wadding 706 is forced out the distal opening of the body 701.

The wadding 706 is scored to form a plurality of nested nibs 709 that are easily separable along score lines. The terminal end of the wadding 707 is coupled with the piston 713 such that, as the piston is displaced in a rotation and/or linear fashion, the wadding is displaced in the same way. Accordingly, the nibs 709 are advanced en masse by turning the knob 715. In some embodiments, once a new nib 709 reaches the proximal end 703 of the body 701, a previous nib 709 simply falls off along the score lines. In some other embodiments, the wadding 706 is scored to a lesser extent and the nibs 709 must be pulled off, pressed off, flicked off, scraped off, or otherwise removed. In addition, a radiopaque thread or similar treatment may be applied to the nibs 709 such that they are easily detectable, thereby allowing easy recovery if lost in an operative field.

In some embodiments of the present technology, the substantially flat end of the most distal nested nib 709' comprises an extended reservoir 710 for holding marking fluid (or similar), thereby preventing the wadding 706 from drying out.

Although the presently described technology has been described in detail with reference to particular embodiments, persons possessing ordinary skill in the art to which this technology pertains will appreciate that various modifications and enhancements may be made without departing from the spirit and scope of the claims that follow. Likewise terms used herein may be coined, and not necessarily terms of art, however, the meaning and scope of such terms will be apparent those skilled in the art in view of the description and figures provided herein.

I claim:

1. A marking apparatus comprising:
   a housing comprising:
      a substantially hollow outer housing with a proximal end and a distal end comprising an end cap for capping the distal end of the outer housing; and
   an inner housing comprising a plurality of writing nibs mechanically constrained in serial alignment within the housing such that the writing tip of the forward-most writing nib extends through an opening at the proximal end of the outer housing, each of the plurality of writing nibs comprises:
      a writing tip comprising an ink selected from xylene-based permanent ink and crystal violet ink, the writing tip extending from a first side away from the writing nib in an axial direction; and
      a cavity disposed in a second side opposing the first side, the cavity configured to accommodate the writing tip of another writing nib, wherein the writing tips of the plurality of nibs are aligned such that the writing tip of a forward-most writing nib extends away from the remaining writing nibs in the serial alignment, whereby the writing nibs are removable from the serial alignment, such that removal of the forward-most writing nib exposes the writing tip of a next-in-line writing nib.

2. The marking apparatus of claim 1, wherein each of the writing nibs comprises a radiopaque treatment.

3. The marking apparatus of claim 1, wherein each of the writing nibs is imprinted with a number.

4. The marking apparatus of claim 3, further comprising a manifest listing a number imprinted on each of the writing nibs in the plurality of writing nibs.

5. The marking apparatus of claim 1, wherein the housing is substantially cylindrical and mechanically constrains the plurality of writing nibs.

6. The marking apparatus of claim 1, wherein the plurality of writing nibs are mechanically constrained by virtue of the writing tips of the writing nibs being serially nested within cavities of another writing nib.

7. The marking apparatus of claim 1, wherein the housing further comprises:

a nib advancement mechanism configured to allow the forward-most writing nib to be removed; and allows advancement of the remaining portion of the plurality of serially aligned writing nibs such that the writing tip of a next-in-line writing nib extends through an opening at the proximal end of the outer housing.

8. The marking apparatus of claim 7, wherein the inner housing further comprises two axial arms mechanically coupled to the end cap and terminating in inward grips.

9. The marking apparatus of claim 7, wherein the nib advancement mechanism comprises a linear channel in the housing.

* * * * *